US00PP21555P3

(12) United States Plant Patent

Fogliani et al.

(10) Patent No.: US PP21,555 P3

(45) Date of Patent: Dec. 7, 2010

(54) APPLE TREE NAMED 'PLFOG99'

(50) Latin Name: *Malus domestica (Borkh.)*
Varietal Denomination: PLFOG99

(76) Inventors: Terry Fogliani, Eagleview Orchard, South Western Highway, Kirup, Western Australia 6251 (AU); Dianne Fogliani, Eagleview Orchard, South Western Highway, Kirup, Western Australia 6251 (AU)

( * ) Notice: Subject to any disclaimer, the term of this patent is extended or adjusted under 35 U.S.C. 154(b) by 41 days.

(21) Appl. No.: 12/214,786

(22) Filed: Jun. 20, 2008

(65) Prior Publication Data

US 2009/0007305 P1 Jan. 1, 2009

Related U.S. Application Data

(60) Provisional application No. 60/937,588, filed on Jun. 27, 2007.

(51) Int. Cl.
*A01H 5/00* (2006.01)

(52) U.S. Cl. ..... Plt./161

(58) Field of Classification Search ..... Plt./161, Plt./172

See application file for complete search history.

*Primary Examiner*—Kent L Bell

(74) *Attorney, Agent, or Firm*—Chris Svendaan

(57) ABSTRACT

'PLFOG99' is a new and distinct apple tree notable for its compact tree type, spur bearing habit, and early maturity as compared to 'Cripps Pink' and other known cultivars.

6 Drawing Sheets

Latin name of the genus and species of the plant claimed: *Malus domestica* (Borkh.).

Variety denomination: 'PLFOG99'.

BACKGROUND AND SUMMARY OF THE VARIETY

The new apple variety 'PLFOG99' originated as a chance limb mutation on a 'Cripps Pink' (U.S. Plant Pat. No. 7,880) apple tree located in a commercial orchard at Kirup, Western Australia in late 1999. The limb was observed to produce fruit up to two weeks earlier than 'Cripps Pink' but also had a significantly different compact growth habit as compared to the 'Cripps Pink' tree. In 2000, ten trees were propagated from the mutated limb by budding onto high vigor 'MM109' apple rootstock, to determine trueness to type as compared with the original limb, for fruit maturity and quality, and compact growth habit. These trees were observed to grow very differently in the field nursery compared with 'Cripps Pink' and other apple trees. The growth type and habit of the trees was columnar and plant growth was compact, with fruit borne on spurs. The first crop, harvested from trees in their third leaf, was very good, yielding approximately 11 kg per tree. These initial promising observations provided the incentive to propagate an additional 100 trees over 4 years for planting from 2002 for further evaluation. Of the 400 trees planted at Kirup, three generations have been observed to be stable and true to type to date. No off-types have been observed. The new variety has been named 'PLFOG99'.

'PLFOG99' is a new and distinct apple tree notable for its compact tree type, spur bearing habit, and early maturity as compared to 'Cripps Pink.'

BRIEF DESCRIPTION OF THE PHOTOGRAPHS

DETAILED BOTANICAL DESCRIPTION

Figure 1:
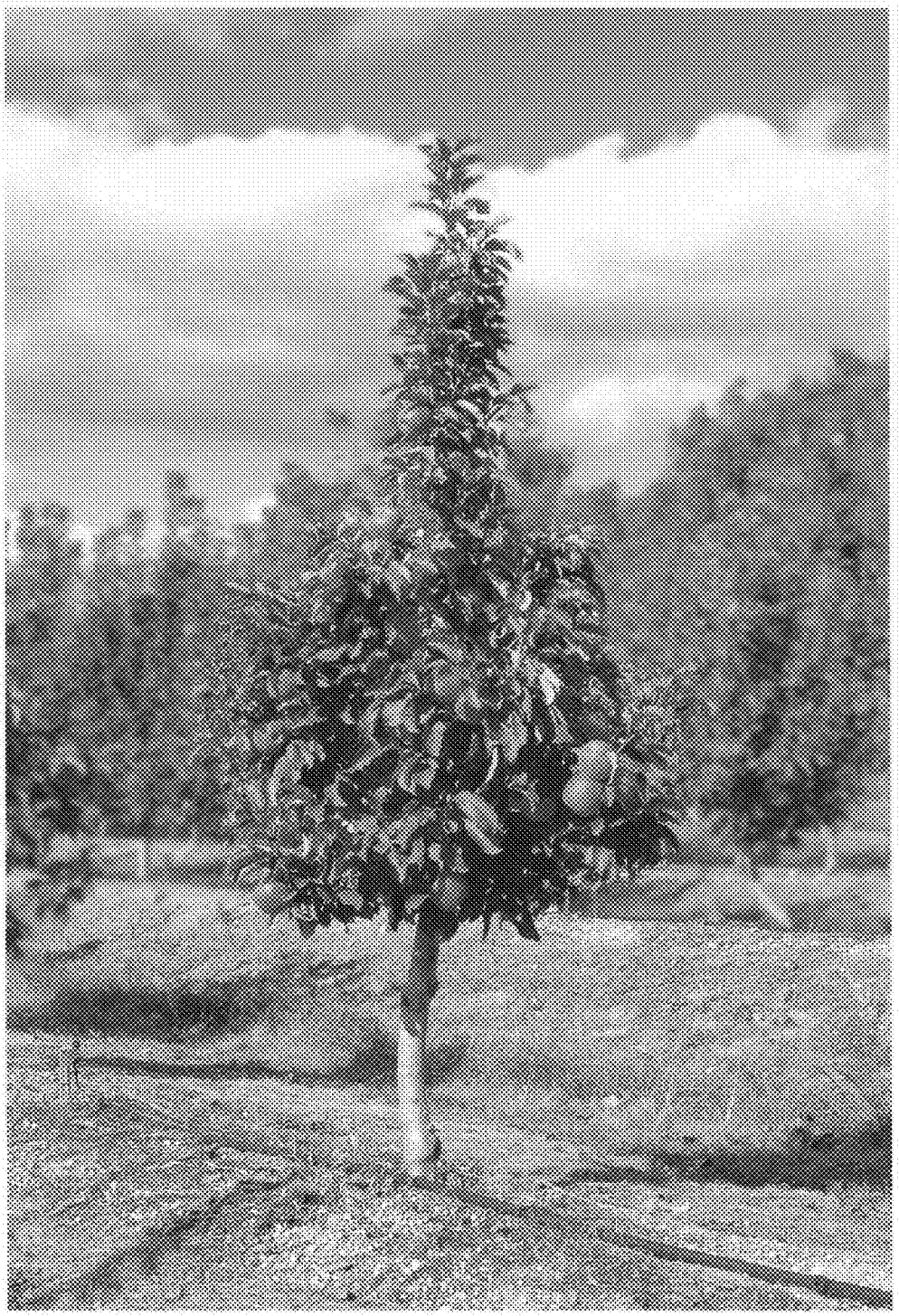
FIG. 1 shows the tree and fruit of the new variety.
Figure 2:
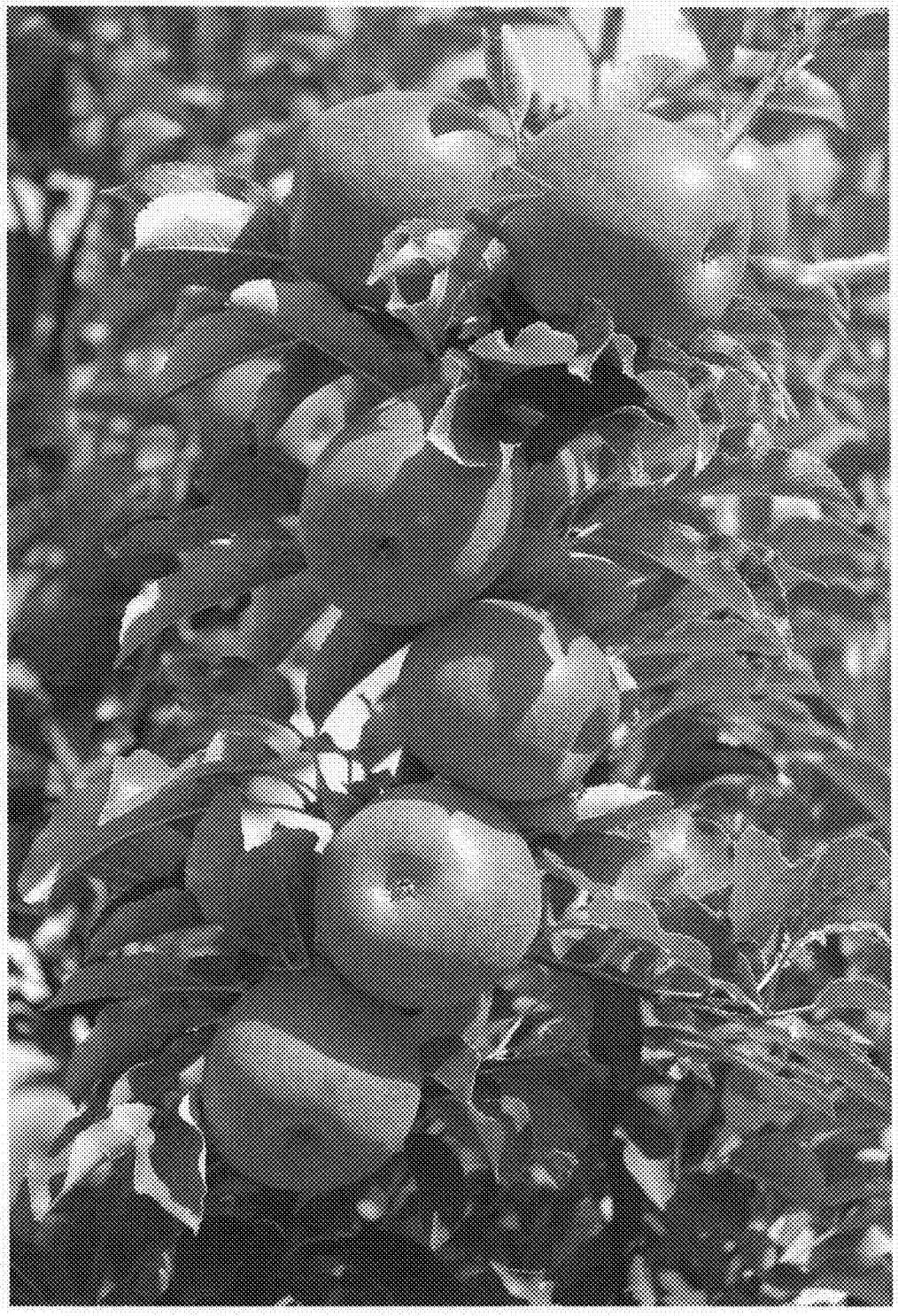
FIG. 2 shows the fruit and leaves of the new variety.
Figure 3:
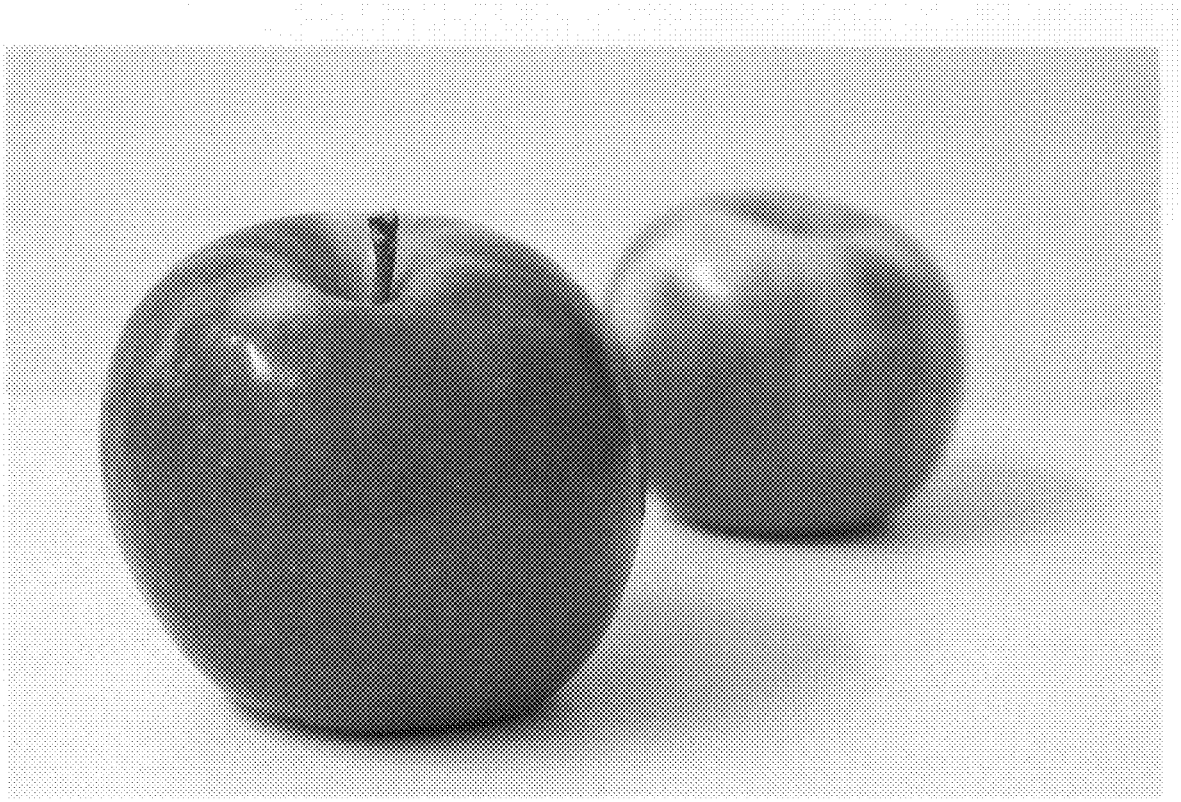
FIGS. 3 and 4 show the fruit of the new variety.
Figure 4:
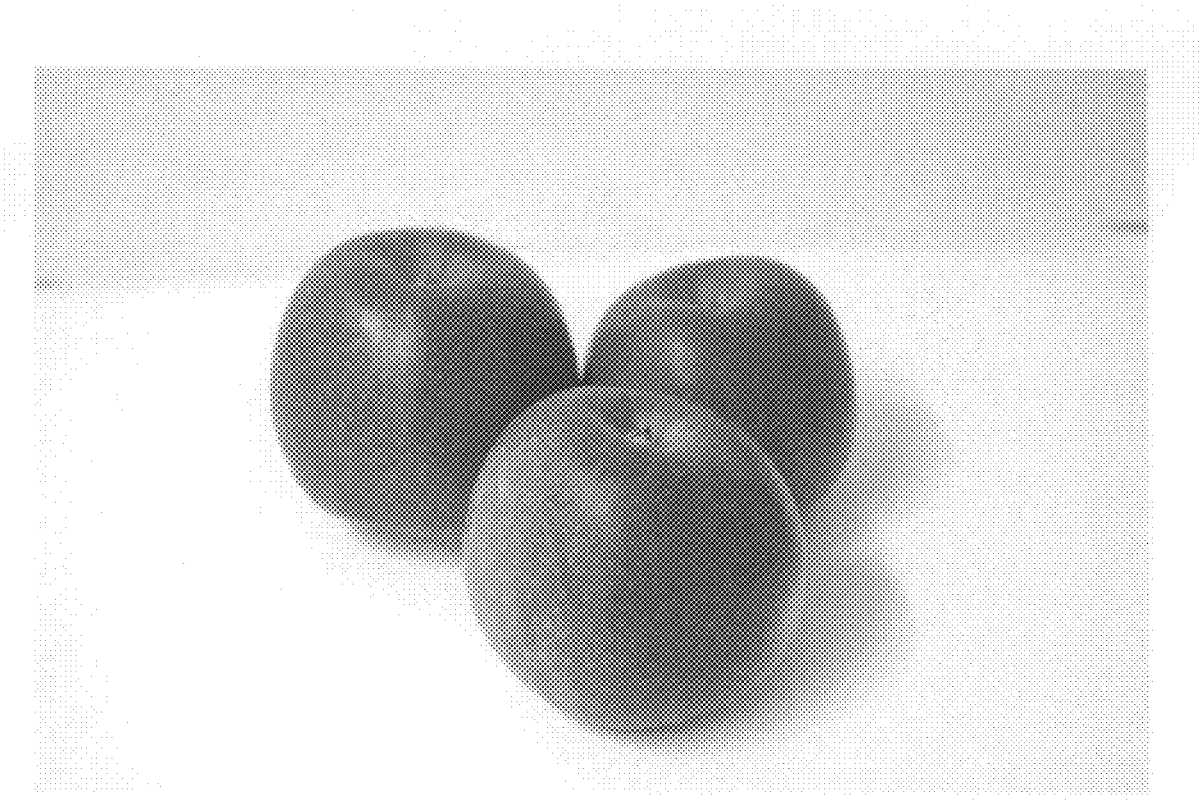
Figure 5:
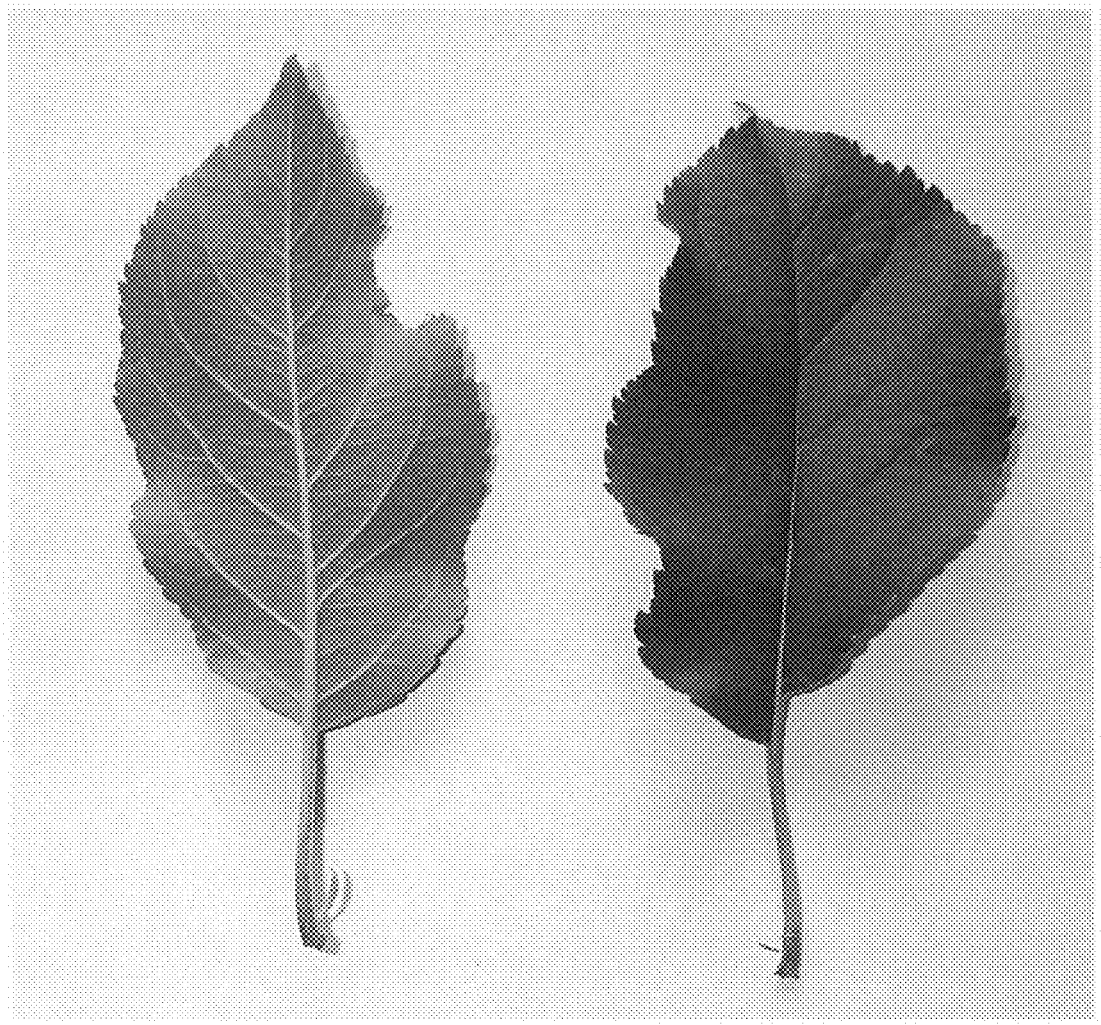
FIG. 5 shows the leaves of the new variety.
Figure 6:
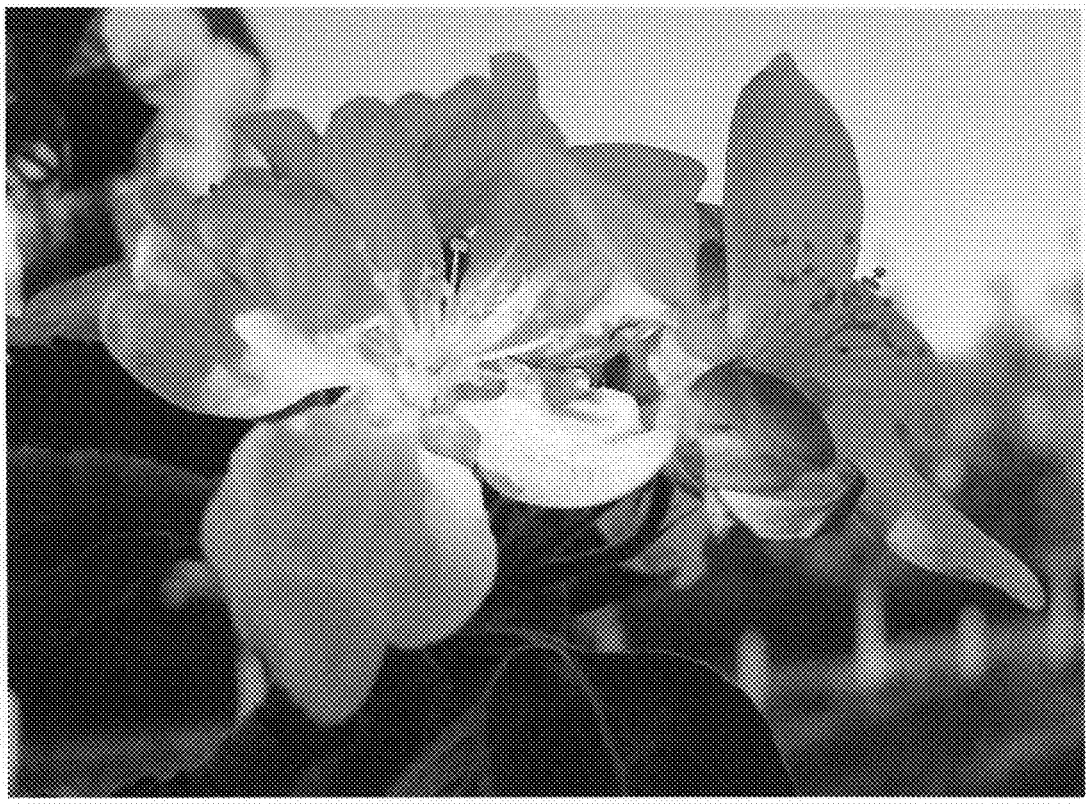
FIG. 6 shows the blossom of the new variety.

The following detailed botanical description is based on observations of $5^{th}$ generation trees planted in 2002, and described during the 2006-2007 and 2007-2008 growing seasons at Kirup, Western Australia. Color descriptions refer to The Royal Horticultural Society Colour Chart (1995). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: Medium to large with dense foliage, upright habit; At maturity, average height is 1.5 m and approximately 1 m spread. Age of described tree 3 years.

Vigor: Low; young trees average less than 80 cm of new growth during the growing season in the nursery row following bud placement.

Trunk: Medium stocky, diameter 6.4 cm at 30 cm above graft union; bark texture smooth; color greenish-brown 165B.

*Lenticels.*—Size 2-3 mm, density 3-4/$cm^2$; color brown 200A.

Branches: Average length 90-100 cm at base of tree; Thick, diameter 2.4 cm; crotch angle relative to the tree trunk 70°; bark smooth; color greenish-brown 165B.

*Lenticels.*—Size 1-2 mm, density 1-2/$cm^2$; color brown 200A.

Chilling requirement: Low to moderate; 500 to 600 hours below 7° C.

Dormant one year old shoot: Pubescence medium; diameter 10 mm; length 60-80 cm; color 165B; internode length 10 mm.

*Lenticels.*—Size 1-2 mm, density 1-2/cm$^2$; color brown 200A.

Flower buds: Quantity per spur 5; Shape round.

*Size.*—Length 8-10 mm, diameter 8-10 mm; Color pink 57A.

Flowers:

*Size.*—Large, diameter 36-40 mm, depth 18-20 mm; Quantity per cluster 4-5.

*Petals.*—Shape: Ovoid to round; Quantity per flower 5; Margins free to touching, smooth; Length 18-20 mm; Width 14-15 mm; Apex shape round; Base shape round; Upper surface color white 155D with traces of pink 67A in veins and edges; Lower surface color white 155D with traces of pink 68A in veins and edges when fully open.

*Sepals.*—Quantity per flower 5; Shape pointed; Length 10 mm; width 3-4 mm; Shape acuminate; Margin straight; Color green 135B.

*Pedicel.*—Length 20 mm; Diameter 2 mm; Color greyed purple 187A.

*Pistil.*—Length 13-14 mm, color green 145B.

*Stigma.*—Width 1 mm, color yellow green 151A.

*Style.*—Length 8 mm, color green 145B.

*Ovary.*—Length 4-5 mm, color greyed purple 187.

*Stamen.*—Quantity per flower 18-22; Filament length 8 mm; Pollen color yellow 5C.

Bloom period: Late; In 2006, first bloom late October, full bloom 28 October; In 2007, first bloom late October, full bloom 4 November (Kirup, Western Australia).

Leaf: Attitude in relation to shoot outwards.

*Size.*—Length 10.5 cm, width 6 cm, length-width ratio 1.75; Shape oval, apex oval, convex, pointed, base round, margin biserrate.

*Color.*—Upper surface RHS 137B, lower surface RHS 147C.

*Petiole.*—Length 35-40 mm, diameter 2 mm, color RHS 141B.

Fruit:

*Size.*—Mass 190 g, diameter 77 mm, height 71 mm, ratio of height to width 0.93.

*Shape.*—General shape in profile Asymmetrical, globose to globose conical, position of maximum diameter middle, ribbing weak; Crowning at calyx end absent or weak.

*Eye.*—Aperture closed or slightly open, depth of eye basin 10 mm, diameter of eye basin 34 mm.

*Stalk.*—Diameter 3 mm-3.5 mm , length 22 mm-28 mm, color greyed purple 185A, depth of stalk cavity 14-15 mm, width of stalk cavity 35 mm.

*Locules.*—Quantity 6, length 11 mm, width 6 mm.

*Lenticels.*—Diameter 0.5-0.8 mm, density 10-14 per square cm.

*Skin.*—Bloom absent or weak, greasiness moderate, ground color yellow-green 154A, overcolor pink-red, 46C, intensity of overcolor medium, percent of overcolor 80-100%, pattern of over color only solid flush.

*Thickness.*—0.7 mm.

*Flesh.*—Texture juicy, firm (8 kg pressure), color cream 155D.

*Seeds.*—Quantity per fruit 5-8, shape obtuse, color dark brown 200A; Aroma distinct, complex and highly aromatic.

*Brix.*—14.3; Yield 40 tonnes/hectare; Use dessert, market.

Harvest date: Late: 2007-May 3; 2008-May 13.

Resistance/susceptibility to known diseases/pests: Unknown.

Keeping quality: Good at 4 months in cold storage (34° F.).

The invention claimed is:

1. We claim a new and distinct apple tree substantially as shown and described herein.

* * * * *